United States Patent [19]

Ubaud

[11] 4,018,362
[45] Apr. 19, 1977

[54] AUTOMATIC CONTROL FOR LIQUID FLOW
[75] Inventor: Patrick Ubaud, Villeurbanne, France
[73] Assignee: Union Chimique Continentale-U.C.C., Puteaux, France
[22] Filed: Nov. 6, 1975
[21] Appl. No.: 629,239
[52] U.S. Cl. .............................................. 222/55
[51] Int. Cl.² ........................................ B67D 5/08
[58] Field of Search ................. 222/55, 76, 63; 141/130

[56] References Cited
UNITED STATES PATENTS

| | | | |
|---|---|---|---|
| 2,604,249 | 7/1952 | Gorham | 141/130 |
| 3,209,795 | 10/1965 | Page | 141/130 |
| 3,252,623 | 5/1966 | Corbin et al. | 222/76 X |
| 3,604,419 | 9/1971 | Diskin et al. | 222/55 X |
| 3,648,694 | 3/1972 | Mogos et al. | 222/55 X |
| 3,655,095 | 4/1972 | Kienitz | 222/76 X |
| 3,887,110 | 6/1975 | Porter | 222/76 X |

Primary Examiner—Stanley H. Tollberg
Assistant Examiner—Hadd Lane
Attorney, Agent, or Firm—Oblon, Fisher, Spivak, McClelland & Maier

[57] ABSTRACT

Automatic regulation system of a flow of liquid, which system comprises an electronic liquid flow control circuit connected to a liquid flow regulation device which it actuates, the said electronic circuit being characterized in that it comprises a drop counting circuit connected to a comparator circuit which comprises a bistable circuit which is itself connected on the one hand to alarm circuits and on the other hand to a monostable circuit, the magnitude of the pulse of which is compared with the magnitude of the pulse of the bistable circuit by means of a comparator circuit to which the bistable and monostable circuits are connected. Said system is used for automatic regulation of the flow of a perfusion liquid.

2 Claims, 6 Drawing Figures

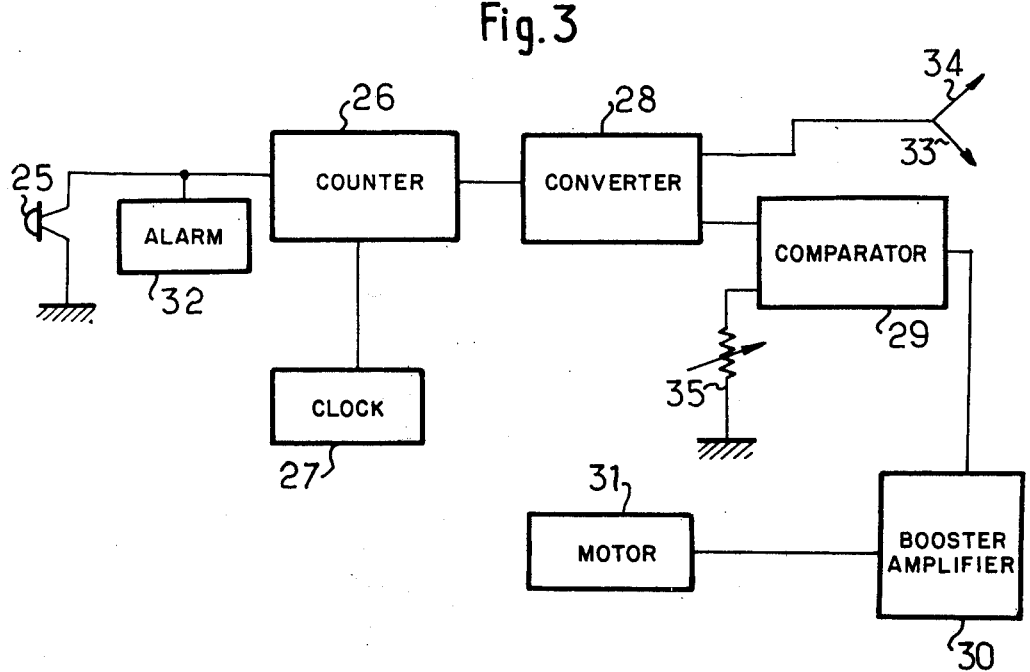
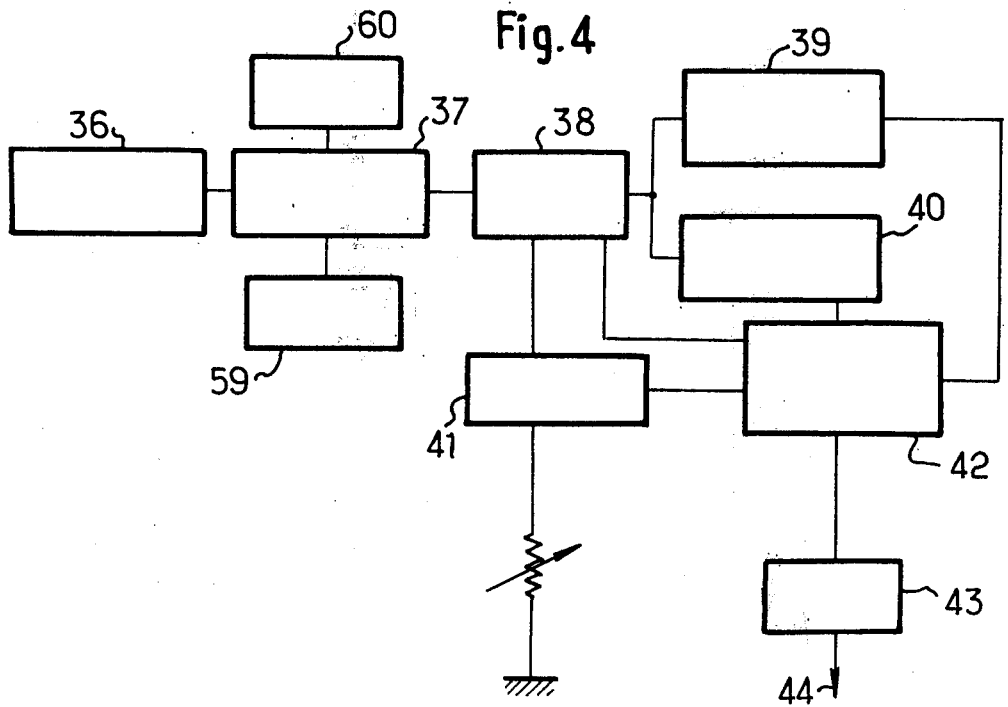

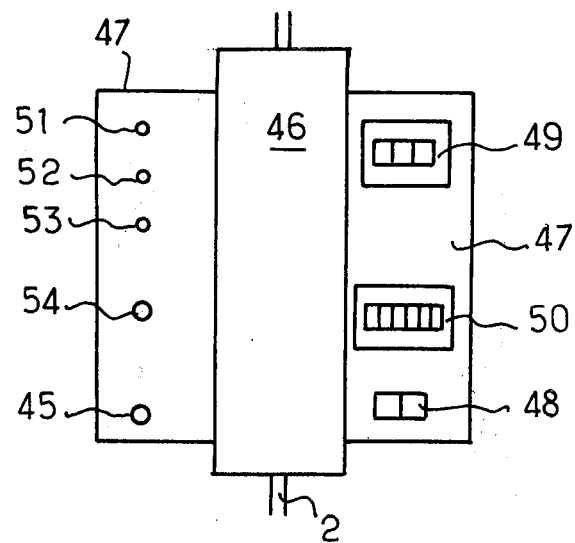
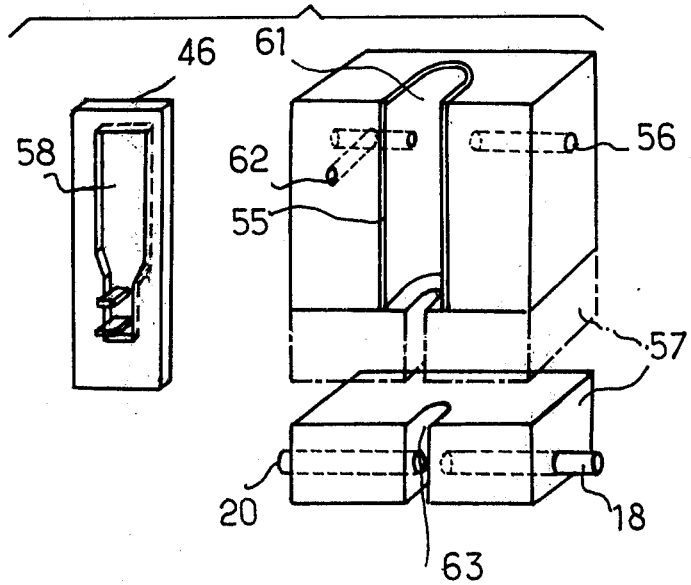

AUTOMATIC CONTROL FOR LIQUID FLOW

BACKGROUND OF THE INVENTION

The present invention relates to a new automatic liquid flow regulation system, and is used in particular for the automatic control of the flow of a perfusion liquid.

As is known, the injection of a patient with medicinal solutions by perfusion is generally carried out by causing a medicinal solution contained in a bottle to flow directly into the patient's vein through a hypodermic needle in the said vein and connected to the bottle via a flexible tube. The perfusion flow is regulated by means of a hand clamp, and as a result there is:

a lack of precision in th flow regulation,
an instability in the regulation due to mechanical or hydraulic alterations in the flow circuit,
the necessity to monitor the flow.

Flow regulation using a hand clamp consequently does not provide any degree of safety for the patient, who runs the risk either of a closure of the supply tube as a result of an accidental contraction of the clamp associated with the said tube, or a release of the clamp which would result in an inadmissible increase in flow.

Attempts have been made to solve this problem by providing the perfusion systems with a peristaltic pump, but it has been found that a satisfactory control of the liquid flow is not obtained since th peristaltic pumps do not ensure an absolutely regular flow and they only ensure a flow above a certain supply threshold.

An apparatus is also known whose purpose is to rhythmically regulate and monitor the distribution of drops in a perfusion line by means of an electronic circuit which acts on a liquid inflow control system in the perfusion line, wherein the said system consists of a microvalve. Although this ensures that the perfusion system operates safely and can be used satisfactorily, the proposed apparatus according to the prior art nevertheless has the disadvantage that it can only operate with a specific perfusion line comprising a drop counting chamber having particular characteristics and connected to the liquid inflow control microvalve: for this reason this apparatus is not a universal type which can be adapted to all perfusion devices; furthermore, the special structure of the drop counting chamber substantially raises the cost price of the apparatus proposed in accordance with the prior art.

There is known by U.S. Pat. No. 3,252,623 an apparatus for monitoring dispensing of a liquid, and more particularly for controlled intravenous feeding and monitoring of drops of liquid material to humans, which apparatus comprises a photocell which provides an impulse corresponding to each drop to be dispensed, said impulse operating a monostable one output of which operates a bistable; an other impulse generator the power of which is a function of the selected number of drops resets the bistable to zero. The main drawback of such an apparatus resides in the fact that the output impulse of the bistable is compared to the output impulse of another monostable the repetition frequency of which is a function of the selected number of drops.

The object of the present invention is consequently to provide an automatic liquid flow regulation system, and in particular for a perfusion liquid, which satisfies the practical requirements better than the previously known flow regulation systems, more particularly in that it provides a regular and very strict automatic regulation of the liquid flow by means of an accurate and relatively simple and cheap piece of apparatus, thereby eliminating any risk of an inopportune interruption in the flow of perfused liquid, for the patient, or of too rapid a flow of liquid, and also obviating the necessity for constant monitoring of the perfusion system and thus the existence of a large number of staff, wherein the apparatus according to the present invention can furthemore be universally adapted to all liquid flow systems and in particular to commercially available perfusion lines.

SUMMARY OF THE INVENTION

The object of the present invention is an automatic liquid flow regulation system, which comprises an electronic liquid flow control circuit connected to a liquid flow regulation device which it actuates, and which is characterized by the combination of an electronic flow control circuit with a liquid flow regulation device consisting of a mechanical closure system for the flexible tube through which the liquid flows, the said system comprising a piston or the like driven by a motor which is itself operated by the flow control device, the said piston or the like exerting a more or less large pressure on the tube as a function of the motor drive, and the said regulation system furthermore comprising alarm circuits.

According to a preferred embodiment of the automatic liquid flow regulation system which forms the object of the present invention, the electronic liquid flow control circuit consists of combining an electronic drop counting circuit with, on the one hand, a pick-up element for the passage of each drop or jet of liquid, such as a photoelectric pick-up of the phototransistor type for example, and on the other hand with a comparator circuit for comparing the number of drops measured with the pre-selected, desired number of drops.

According to an advantageous arrangement of this embodiment, the drop counting circuit comprises a monostable circuit connected on the one hand to a comparator consisting of an integrator and a differential amplifier, and on the other hand to a display system for the number of drops measured.

According to another advantageous arrangement of this embodiment, the drop counting circuit comprises a monostable circuit connected to a comparator circuit comprising a bistable circuit which is itself connected on the one hand to alarm circuits and on the other hand to another monostable circuit, the pulse from which is compared with the pulse of the bistable circuit by means of a comparator to which the bistable circuit and the said monostable circuit are connected.

According to another advantageous embodiment of the automatic liquid flow regulation system in accordance with the present invention, the electronic flow control circuit consists of combining a digital counter which counts the pulses delivered by the pick-up as a function of the number of drops flowing in a liquid flow tube whose flow rate is controlled with, on the one hand, a clock which supplies pulses for a specific time corresponding to the duration of counting, and, on the other hand, a digital analogue converter which provides a direct current voltage proportional to the number of drops flowing, which voltage is compared in a comparator connected to the digital analogue converter with a reference voltage proportional to the desired number of drops.

According to a preferred embodiment of the object of the invention, the drive motor for the piston or the like for closing the flexible tube through which the liquid flows is operated by the comparator of the liquid flow control device.

In accordance with the invention, the actuation of the drive motor for the piston or the like is effected by means of an electrical actuating element for the motor, such as a booster amplifier for example.

In accordance with the present invention, the automatic liquid flow regulation system, the liquid reservoir and the flexible tube, like the perfuser for example which is subjected to the liquid flow regulation, are arranged in a compact unit.

According to an advantageous embodiment of the compact unit, which also forms one of the objects of the present invention, this latter comprises a solid housing in which are arranged the electronic circuits for the liquid flow regulation, the Photoelectric pick-up and the light source, and also the mechanical liquid flow regulation device, and the said housing contains an indicator and control panel for the regulation system and comprises a suitably shaped recess to receive a removable and interchangeable reservoir holder which can be removed and changed as a function of the volume of the perfuser.

According to an advantageous embodiment of the compact unit of the present invention, the liquid reservoir is arranged, together with the flexible liquid flow tube, in a recess adapted to receive them and located in a cover which covers the whole of the compact unit.

In addition to the preceding arrangements, the invention also comprises other arrangements which will become evident from the following description.

The invention is more particularly directed to new automatic liquid flow regulation systems in accordance with the preceding arrangements, and also to means adapted to provide and carry out these systems and the installations in which the said regulation systems are included.

BRIEF DESCRIPTION OF THE DRAWINGS

The invention will be better understood with the help of the remainder of the description which follows, and which refers to the accompanying drawings in which:

FIGS. 2 to 4 are circuit diagrams of various embodiments of the automatic regulation system according to the present invention, FIG. 5 is a front view of the part of the compact unit forming the object of the present invention, which comprises the recess for the liquid reservoir and the indicator and control panel of the regulation system, and FIG. 6 is a longitudinal section of a compact unit in accordance with the arrangements of the invention.

However, it should of course be understood that these drawings and the corresponding descriptive sections are given purely as an illustration of the object of the invention, and are in no way a limitation thereof.

DESCRIPTION OF THE PREFERRED EMBODIMENTS

Figure 1:
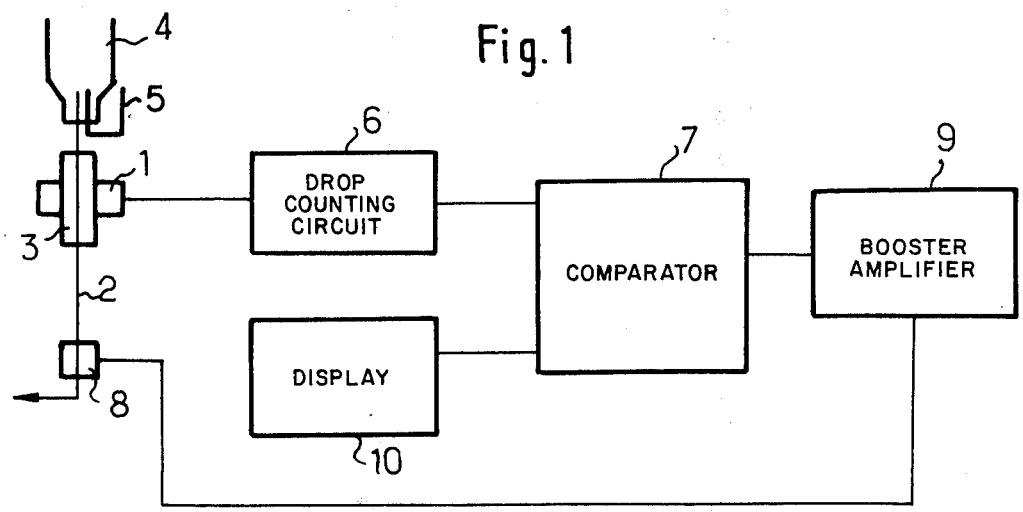
FIG. 1 is an outline diagram of the automatic regulation system forming the object of the present invention.

According to the invention, the general outline diagram shown in FIG. 1 comprises a pick-up 1 connected to the liquid flow tube 2, preferably via a drop counting chamber 3 carried by the flow tube 2, the latter being connected to a reservoir 4 of liquid advantageously provided with an air removal tube 5 which helps to ensure a perfect flow of the liquid from the reservoir 4 to the tube 2.

The pick-up 1 is connected to a drop counting circuit 6 which advantageously consists of a suitable electronic circuit system; the pick-up 1 converts each passage of a drop or jet of liquid into an electrical voltage which feeds the drop counting circuit 6. The number of drops measured by the circuit 6 is compared with the preselected, desired number of drops by means of a comparator 7 which delivers a reference voltage proportional to the preselected, desired number of drops. If there is no coincidence between the number of drops measured and the desired number of drops, the difference between these two values actuates a liquid flow regulation device 8 which is secured to the liquid flow tube 2. The comparator 7 and the liquid flow regulation device 8 are advantageously connected to one another via a booster amplifier 9.

The pick-up for the passage of drops may consist for example of an arrangement comprising a photoelectric cell operating in the red and infra-red regions of the spectrum, which is not affected by the ambient light.

The pre-selected number of drops is the object of a display arrangement 10 connected to the comparator 7, and is shown on the control panel of the regulation system which forms the object of the present invention.

Figure 2:
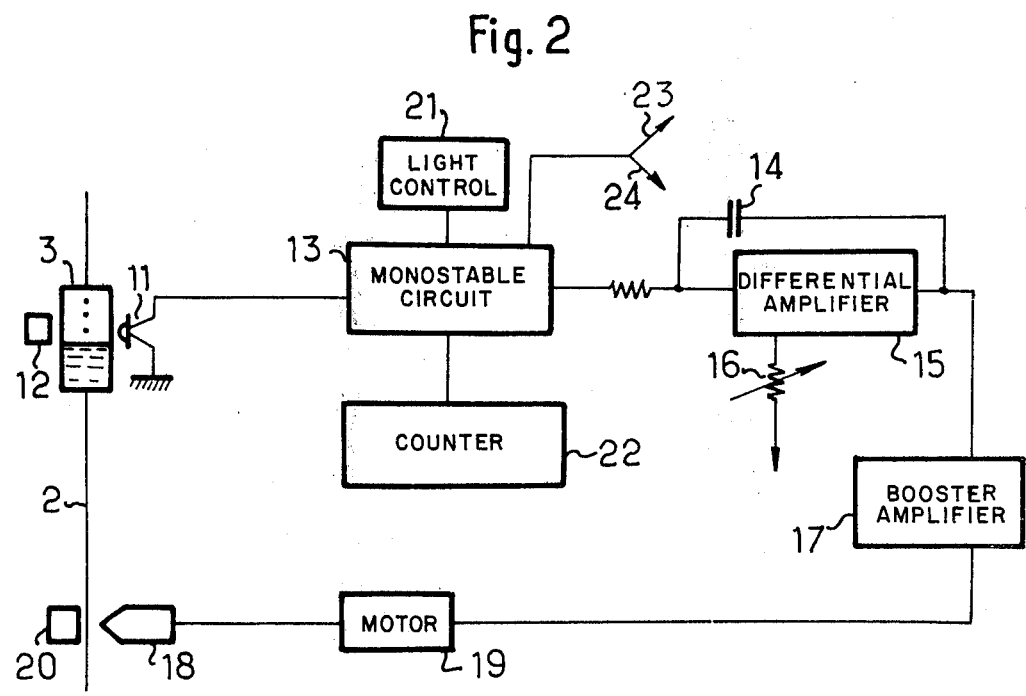

In the embodiment of the object of the invention shown in FIG. 2, the pick-up consists of a phototransistor 11 placed at the level of the drop counting chamber 3 arranged on the liquid flow tube 2, and opposite a source 12 of red light. The phototransistor 11 is connected to a transistor circuit system 13, such as that known by the term "monostable" circuit, which passes from an unstable state produced by a pulse applied to the inlet and after a specified period of time then spontaneously returns to a stable state. The output pulses from the monostable circuit 13 are integrated by the integrator 14 which acts as a comparator in combination with the differential amplifier 15 connected to the reference display circuit 16. The unit consisting of the integrator 14 and the differential amplifier 15 is connected, via the booster amplifier 17, to a liquid flow regulation device which regulates the flow of the liquid in the flexible tube 2, and the said device advantageously consists in accordance with the invention of a mechanical system for squeezing the tube, such as the piston 18, which is operated by a servomotor 19. The tube squeezing piston 18 actively cooperates with a counter-plate 20 for the fine regulation of the squeezing of the tube 2, the said counter-plate 20 being located opposite the piston 18 and the mechanical units 20 and 18 being placed on both sides of the tube 2.

The operation of the circuit shown in FIG. 2 is a follows:

Each passage of a drop interrupts the rays of red light from the source 12 with the result that the phototransistor 11 delivers a pulse which triggers the monostable circuit 13, and the output pulses therefrom are integrated by the integrator 14 to give, at the outlet of the latter, a voltage proportional to the preselected desired number of drops. Thus, if the voltage given by the monostable circuit 13 and the voltage from the comparator are equal at the inlet of the booster amplifier 17, the voltage at the outlet is zero and the motor 19, which operates by direct current, does not receive any voltage and consequently does not turn: the system is in equilibrium.

If on the other hand the measured number of drops is for example greater than the preselected number of drops, the voltage at the outlet of the booster amplifier 17 is positive and the motor turns in a direction which drives the piston so as to partially squeeze the tube, thereby reducing the flow rate of the drops.

Likewise, if the number of drops is less than the preselected number, the voltage at the outlet of the booster amplifier 17 becomes negative and drives the motor 19 so as to rotate in a direction which withdraws the piston and dilates the diameter of the tube so as to assist the flow of liquid therein.

At each passage of a drop the monostable circuit 13 triggers a light control 21 and also an aggregate counter 22 for the number of drops, which may be an addition-subtraction device which stops the flow of liquid when the preselected, desired total number of drops is obtained.

The monostable circuit 13 also operates two alarm controls 23 and 24 respectively when the flow has stopped or has become too great.

In the embodiment of automatic liquid flow regulation system shown in FIG. 3, the pick-up for the passage of the drops of liquid namely the phototransistor 25, cooperates with a digital counter 26 which counts the pulses from the phototransistor 25 for a time determined by the pulses supplied by the clock 27; a digital-analogue converter 28 gives a direct current voltage which is proportional to the number of drops measured by the digital counter 26. The voltage given by the converter 28 is compared with a reference voltage which is proportional to the desired number of drops and is given by the comparator 29, which latter is connected to a reference display circuit 35 for the predetermined number of drops.

The piston or the like for regulating the flow is actuated, in the case where the above two voltages are different from one another, by means of a booster amplifier 30 and a drive motor 31.

The converter 28 operates two visual and/or acoustical alarms 32-33, one in the case of a stoppage in the flow and the other in the case of an excessive flow. A light control 34 is operated by the digital counter 26 at each passage of a drop.

The embodiment of automatic liquid flow regulation system shown in FIG. 4 uses a monostable circuit 37 for counting the drops, which acts under the effect of pulses delivered by the phototransistor 36, which is itself operated by the interruption of a bundle of light rays in the rhythm of the passage of the drops in the flow tube. The time between two drops is converted into a voltage square wave by a bistable circuit 38 connected to alarm circuits 39 and 40 which will be discussed hereinafter.

The bistable circuit 38 is furthermore connected to a monostable circuit 41, the magnitude of the output pulse from which is regulated in accordance with the desired number of drops. This pulse is compared by the comparator 42 to the pulse delivered by the bistable circuit 38.

When the time between two drops is equal to the pulse delivered by the monostable circuit 37 (which is connected to a display circuit 59 for the number of drops "subtracted" or to a display circuit showing the actual time between the flow of two successive drops, as well as to a light control 60 which lights up at each passage of a drop), the voltage at the outlet of the comparator 42 is zero: the system is in equilibrium.

When the time between two drops is greater than the time shown (displays) (or greater than the desired number of drops), the comparator 42 gives a pulse at its outlet, which is positive for example, which drives the motor 44 (by means of the amplifier 43) in the direction so as to open the tube. In the opposite case the pulse delivered is negative and the motor turns in a direction which closes the tube.

In the case where it is impossible to effect any degree of regulation, for example if the flow rate is less than one drop per minute or greater than 150 drops per minute, the monostable circuit operates the alarm circuit 39 or the alarm circuit 40.

As soon as the alarm 40, which corresponds to too great a flow (greater than 150 drops/minute for example) is operated, an electromagnetic clamp device (not shown) or any similar suitable system closes the liquid flow tube.

It is advantageous to provide the system which an inverter 45 which, at the moment when the regulation system according to the invention starts to operate, controls the opening of the flow regulation piston so as to be able to introduce the liquid flow tube into its compression zone.

In accordance with the invention, the automatic liquid flow regulation system is mounted together with the liquid reservoir and the liquid flow tube in a compact unit such as is shown in FIGS. 5 and 6.

The compact unit according to the present invention advantageously comprises four parts, namely:

1. A solid housing 46-47-57 whose upper part 47 contains the indicator and control panel for the automatic regulation system according to the invention, said panel containing a stop-start button 48 and the inverter 45 which, at the start, controls the opening of the piston 18 so as to be able to place the liquid flow tube 2 therein; it also comprises a display counter 49 for the desired, preselected number of drops, as well as a counter-subtractor 50 for the number of drops measured; it also contains light indicators, namely the control 51 which lights up at each passage of the drops, and the light alarms 52 and 53 which light up respectively in the absence of any flow and in the case where the flow is too great. A stop button 54 for sound alarms is also provided on the display and control panel.

The upper part 46-47 of the solid housing contains the electronic circuits, the preferred embodiments of which have been shown by way of non-limiting examples in FIGS. 1 to 4, and also the photoelectric pick-up and the light source.

2. The part 46 of the solid housing is a door which conceals a recess 55 in which a reservoir holder 61 can just fit, and the said holder can be removed and changed as a function of the volume of the liquid reservoir (not shown). This reservoir holder 61 is made of any suitable material, such as plastics material for example. The compact unit 47-55-61 comprises holes arranged opposite one another to allow light rays to pass through. A control orifice 62 in the part 46 is oriented perpendicularly to the orifices 56 and opens into the passage formed by the said orifices 56, and enables the passage of light in the latter to be controlled.

3. The lower solid part 57 is integral with the upper part 47-55 of the housing and is distinguished from the latter by the fact that it comprises a recess 63 for the passage of the liquid flow tube 2: this part 57 contains the liquid flow regulation piston 18 in the tube 2, and also the fine regulation counter-plate 20 for squeezing the liquid flow tube 2.

4. The door 46, which is of a transparent material such as "Plexiglass" for example, covers the recess 55-61 of the solid housing as well as the portion of the lower part 57 of the said housing which is in the extension of the recess 55-61.

The interior of the door 46 is provided with a recess 58 for receiving liquid reservoir (not shown) as well as the tube 2.

The compact unit 46-47-57 according to the present invention contains, within a restricted space, the electronic regulation circuits, the control and regulation means, as well as the drive means and flow means and also the liquid reservoir and the flow tube for the latter, and thus provides a strong and stable apparatus all the parts of which are protected and whose operation is simple, reliable and precise, and which can be used universally since it can be employed with the commercially available perfusion units without having to alter the latter in any way whatever.

The automatic liquid flow regulation system which is the object of the present invention is particularly suitable for controlling perfusion liquids administered to patients, but it goes without saying that it is suitable in all cases where it is necessary to ensure a regular and constant flow of liquid, such as is the case for example when adding a reagent drop by drop to a given reaction medium in order to carry out chemical reactions.

It follows from the preceding description that irrespective of the embodiments and methods of application which are adopted, automatic regulation systems for liquid flow are obtained which have important advantages compared with previously known regulation systems for the same purpose, certain of which advantages have been mentioned in the preceding description, among which one may mention the advantage of allowing a much more precise operation than the heretofore known apparatuses, and the advantage of providing an apparatus in which the output impulse of the bistable is compared to the output impulse of a monostable the width of which is a function of the selected number of drops.

As is clear from the preceding description, the invention is not restricted solely to those embodiments and methods of application which have just been described in detail; on the contrary, it also covers all the variations which can be envisaged by one skilled in the art without departing from the scope or subject matter of the present invention.

What I claim is:

1. A system for automatically regulating liquid flow comprising:
    a piston;
    a counter-plate;
    a flexible tube for conveying a liquid, the tube being positioned between the piston and the counter-plate;
    a photoelectric pick-up connected to the tube for detecting the passage of drops of the liquid therethrough;
    a first monostable connected to and operated by the photo-electronic pick-up for counting the drops of the liquid passing through the tube;
    a bistable connected to the first monostable and responsive to the counting of the first monostable for supplying an output pulse of duration equal to the time interval between the passage of consecutive drops of the liquid through the tube;
    a second monostable connected to the bistable for supplying an output pulse of regulatable duration;
    a comparator connected to the bistable and to the second monostable for comparing the duration of the output pulses of the bistable and the second monostable;
    an amplifier connected to the comparator and activated thereby when the comparator signifies a mismatch between the duration of the output pulses of the bistable and the second monostable; and
    a bi-directional motor connected to the amplifier and activated thereby for moving the piston to squeeze the tube against the counter-plate to regulate the flow of drops of liquid passing through the tube.

2. The system for automatically regulating liquid flow recited in claim 1 including:
    a compact housing enclosing the piston, counter-plate, tube, photo-electric pick-up, first and second monostables, bistable, comparator, and amplifier, the housing having a recess for receiving a replaceable liquid reservoir adapted for coupling to the tube, and a door for concealing the recess; and
    a control panel contained in the housing.

* * * * *